Jan. 22, 1974 B. J. MACHIN Plant Pat. 3,444
CHRYSANTHEMUM PLANT
Filed Dec. 27, 1971
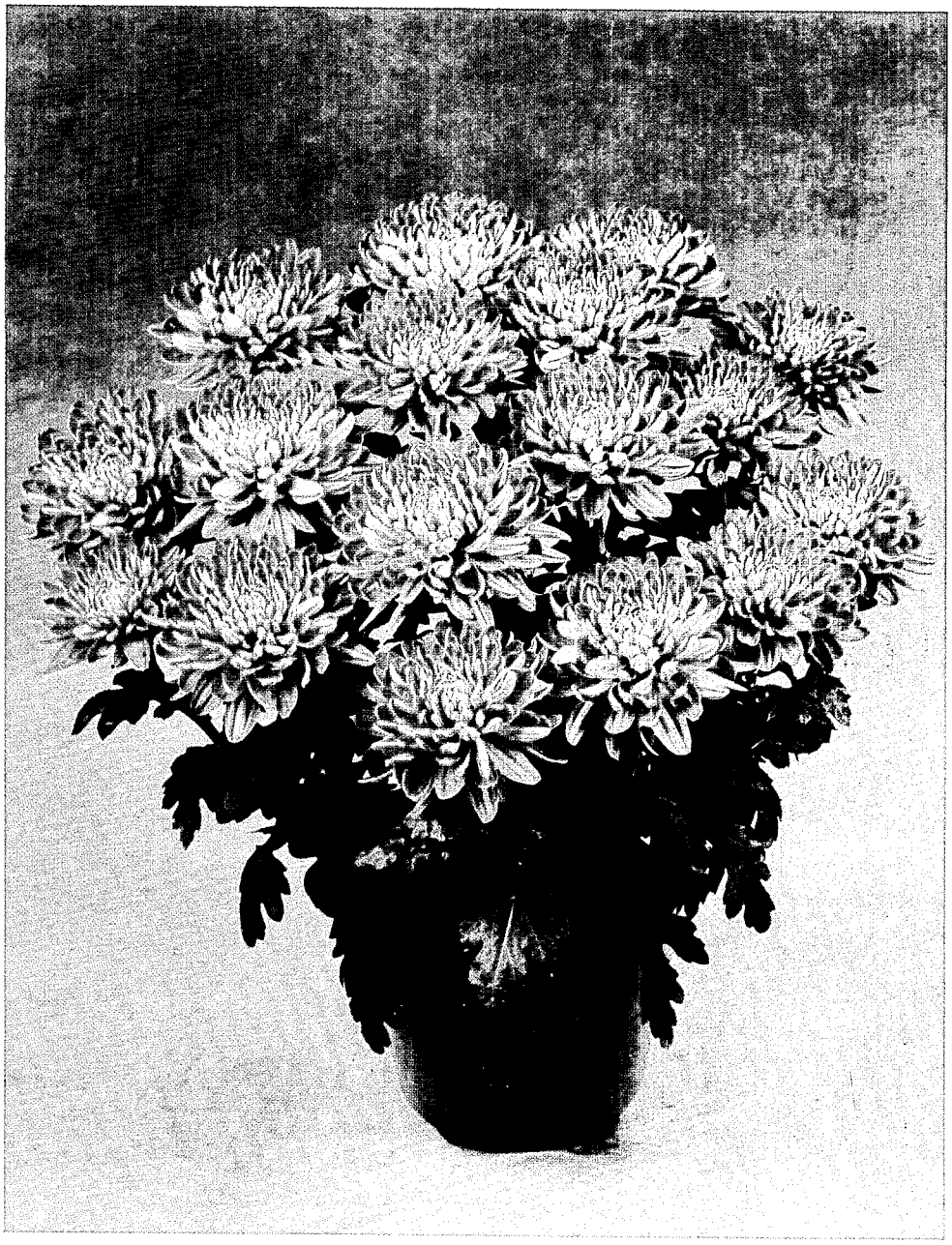

United States Patent Office

Plant Pat. 3,444
Patented Jan. 22, 1974

3,444
CHRYSANTHEMUM PLANT

Barrie John Machin, East Broyle Estate, Chichester, England, assignor to Frampton's Nurseries Limited, Chichester, Sussex, England Filed Dec. 27, 1971, Ser. No. 212,835
Int. Cl. A01h 5/00
U.S. Cl. Plt.—82 1 Claim This invention relates to a new and distinct variety of *Chrysanthemum morifolium* Bailey, pot type, known as Port Magnum.

Port Magnum is a sport from a seedling originated by me from an unpatented cross made in 1966 between the variety Redcap and the unpatented variety Frolic, the former being the seed parent, the latter being the pollen parent.

The variety Magnum resulted from an extensive breeding program with the object of producing improved varieties of year round pot chrysanthemums, with more uniformity and better response under poor light conditions as compared with existing varieties.

Port Magnum is a sport produced in November 1969 by irradiation from the variety Magnum in cultivated ground at Frampton's Nurseries, Ltd., Forbridge Nursery, Chichester, Sussex, England.

Port Magnum is distinguished from Magnum by its distinct ruby color (RHS 60B) as compared with the fuchsia purple (RHS 67A) of Magnum.

As compared with the seed parent of Magnum, Port Magnum is mauve rather than red, has larger, more luxuriant foliage, produces more shoots after pinching, which flower in a more uniform manner, and makes a better pot plant.

As compared with the pollen parent of Magnum, Port Magnum has a larger flower size and a deeper color.

Both Magnum and Port Magnum are distinguished from the Princess Anne varieties, the most similar chrysanthemums with which I am familiar, by the following improved characteristics:

(1) Due to a shorter internode length, the height of plant can be controlled more easily using day length or chemical dwarfing control measures.
(2) Although the flowers are smaller, the incurving form is much improved and more flowers per plant are obtained.
(3) The intense colors are not available in the Princess Anne range of varieties. The color of Port Magnum is not available in any modern pot plant variety.
(4) Response is much more uniform under poor winter light condition.

Asexual reproduction of this new variety Port Magnum by rooting vegetative shoots at Chichester, Sussex, England, shows that the above characteristics are fixed and come true to type through succeeding generations.

The accompanying drawing shows a typical flower of my new variety in color as nearly true as it is reasonably possible to make the same in a color illustration of this character.

The following is a detailed description of the new variety Port Magnum with color terminology in accordance with the Royal Horticultural Society color chart hereinafter referred to as RHS.

Genus: Chrysanthemum
Species: *Morifolium* Bailey
Type: Pot
Class: Incurving decorative
Breeding: The original seedling resulted from a cross between the varieties Redcap and Frolic, the former being the seed parent, and the latter being the pollen parent. The cross was made in 1966 at Frampton's Nurseries Ltd., Forbridge Nursery, Chichester, Sussex, England.
Propagation: Holds its distinguishing characteristics through succeeding propagations by rooting vegetative shoots.
Flower: When grown and observed in Sussex, England, in 3½ inch pots and pinched, up to six flowers per plant are formed. When five plants are planted per 5 inch pot, 4 to 5 flowers are borne on each plant.
Bloom:
*Size.*—Average diameter is 8 to 9 cms. when fully open.
*Petalage.*—Incurving decorative with approximately 170 to 200 ray petals and five disc petals.
*Form.*—Incurving decorative.
*Petals.*—Long, broad, overlapping, blunt, flat and of medium texture.
Color of open bloom:
Inner face of fully expanded petal, RHS 60B
Outer face of fully expanded petal, RHS 13A streaked with RHS 60B
Inner face of young petal, RHS 60A
Outer face of young petal, RHS 13A streaked with RHS 60B
Response Group: 10 weeks
Temperature tolerance: 55–60° F. at night.
Plant: Stocky well branched habit of growth.
Foliage:
Good quality, average internode length 1½ to 2 cm. Medium size—color RHS 137B, medium texture.
Stem: Thick and strong. Color, RHS 145C at flowering.

I claim:

1. A new and distinct variety of *Chrysanthemum morifolium* Bailey, pot type, substantially as herein shown and described, characterized particularly as to novelty by the unique combination of a uniform response under winter light conditions, a short internode length, incurved flowers, and a distinct ruby color.

No references cited.

ROBERT E. BAGWILL, Primary Examiner